United States Patent [19]
Peifer

[11] Patent Number: 6,096,264
[45] Date of Patent: Aug. 1, 2000

[54] TOOTHBRUSH STERILIZATION CABINET

[76] Inventor: Melvin W. Peifer, R.R. 2, Box 349-H, Millville, Pa. 17846

[21] Appl. No.: 09/111,382

[22] Filed: Jul. 7, 1998

[51] Int. Cl.$^7$ ........................................................ A61L 2/10
[52] U.S. Cl. .......................... 422/1; 422/24; 250/455.11; 30/541; 206/351; D6/526; D6/528
[58] Field of Search .................................. 422/24, 1, 300; 250/455.11; 30/34.05, 45, 537, 541, DIG. 1; 206/351; D6/526, 528, 534

[56] References Cited

U.S. PATENT DOCUMENTS

| | | |
|---|---|---|
| 3,633,089 | 1/1972 | Dorion, Jr. et al. . |
| 4,772,795 | 9/1988 | Sakurai et al. . |
| 5,259,083 | 11/1993 | Stansbury, Jr. ............................ 15/22.1 |
| 5,459,322 | 10/1995 | Warkentin ........................... 250/455.11 |
| 5,487,877 | 1/1996 | Choi ....................................... 422/24 X |
| 5,688,475 | 11/1997 | Duthie, Jr. ............................ 422/186.3 |
| 5,699,575 | 12/1997 | Peifer ................................... 422/300 X |
| 5,727,273 | 3/1998 | Pai ........................................... 15/22.1 |

FOREIGN PATENT DOCUMENTS 29701302  7/1997  Germany .

*Primary Examiner*—Elizabeth McKane
*Attorney, Agent, or Firm*—Terrance L. Siemens

[57] ABSTRACT

A sterilizing cabinet for storing and sterilizing personal toilet articles, such as toothbrushes. The cabinet has a housing including a swinging door, receptacles for receiving and supporting a variety of differently configured electrically operated toothbrushes, and a rack having holes or slots for receiving and supporting manual toothbrushes. The cabinet has an electrical system having and supplying a sterilizing lamp capable of emitting ultraviolet radiation, an illuminating lamp capable of emitting visible light, and an AC-to-DC converter connected to recharging elements disposed within the receptacles for receiving electric toothbrushes. The sterilizing and illuminating lamps are independently switched. A safety switch senses door closure, and breaks power to the sterilizing lamp when the door is open. A charging receptacle connected to the AC-to-DC converter is mounted on the exterior of the cabinet.

9 Claims, 2 Drawing Sheets

TOOTHBRUSH STERILIZATION CABINET

BACKGROUND OF THE INVENTION

1. Field of the Invention

The present invention relates to sterilizing apparatus for personal articles, such as toothbrushes, and more particularly to cabinets for storing and sterilizing plural personal articles. The novel enclosure has apparatus for enclosing and sterilizing articles by exposure to ultraviolet light, and apparatus for recharging diverse battery operated personal appliances, such as electric toothbrushes.

2. Description of the Prior Art

Personal articles, such as toothbrushes, hair brushes, razors, and the like are susceptible to being exposed to bacteria, viruses, spores, and other microbes. This holds true even if stored in a container or cabinet. It is therefore possible for an individual using these articles to become exposed to infection.

One answer to this problem is to provide storage containers and cabinets with sterilizing apparatus, such as lamps capable of emitting ultraviolet light (UV) or other electromagnetic radiation harmful to microbes. This approach is seen in U.S. Pat. No. 5,487,877, issued to Min K. Choi on Jan. 30, 1996. The patent to Choi describes a general purpose sterilizer for storing and sterilizing diverse personal toilet articles. However, Choi's device is configured to contain only one type of certain appliances, whereas the present invention contemplates accommodation for diverse varieties of a single type of appliance. This is particularly true for recharging equipment, which in the present invention offers both direct contact of electrodes and also inductive charging. Choi, by contrast, offers but a single type of charger in his invention. Also, Choi stores many devices out of range of UV radiation, some exposed to the exterior of the device, whereas all devices stored in the present invention are contained within the enclosure and are exposed to UV radiation.

U.S. Pat. No. 5,459,322, issued to Kenneth Warkentin on Oct. 17, 1995, describes a cabinet partially lined with UV emitting lamps. Switches are provided to selectively vary intensity of and to de-energize some lamps. The device of Warkentin lacks the recharging features found in the present invention, and thus would be unsuited to recharge as well as sterilize electric toothbrushes. Also, the device of Warkentin lacks the various holders provided in the present invention for holding diverse personal articles during storage and sterilization.

U.S. Pat. No. 4,772,795, issued to Masatoshi Sakurai et al. on Sep. 20, 1988, and U.S. Pat. No. 5,688,475, issued to Robert E. Duthie, Jr. on Nov. 18, 1997, describe sterilizers which emit UV radiation and hold dental equipment in respective sterilizing chambers. The devices of Sakurai et al. and Duthie, Jr. lack recharging features and diverse specially configured holders or receptacles for holding diverse personal articles.

None of the above inventions and patents, taken either singly or in combination, is seen to describe the instant invention as claimed.

SUMMARY OF THE INVENTION

The present invention provides a cabinet which can store and sterilize a variety of personal toilet articles. An important feature of the invention is that it accommodates different commercial examples of a single category of equipment, and is therefore usable with many different commercial products. Illustratively, many electrically operated toothbrushes are commercially available. These toothbrushes vary in dimensions and configuration, and also in method of recharging their batteries. For toothbrushes and other electrical appliances, such as electric razors, recharging may be accomplished through exposed electrodes, or alternatively by induction. Exposed electrodes may vary in location and dimensions. Some may be recessed while others protrude from the associated appliance. Appliances utilizing induction recharging may also differ in location and dimensions of their induction coils.

The present invention solves the problem of recharging while not limiting the user to a particular one appliance by providing a variety of receptacles and recharging facilities. These receptacles and facilities preferably conform to those varieties of electrical appliances which are currently commercially available and widely distributed.

In another aspect, the present invention provides a single housing enclosing a large sterilizing chamber in which articles being stored and sterilized are housed. Several electric toothbrushes, manual brushes, and hair utensils are stored in common in the sterilizing chamber. A variety of receptacles and holders are provided for this purpose.

Electricity is supplied to the cabinet by a plug and cord preferably protected by an integral ground fault interrupter. The sterilizing chamber has a lamp for providing UV radiation, and a second lamp providing visible light for purposes of general illumination. The two lamps are independently switched. A door switch interrupts power to the UV lamp when the door is open to protect users. A battery charger connected to the power supply is externally mounted on the cabinet.

Accordingly, it is one object of the invention to provide a cabinet for storing and sterilizing personal toilet articles.

It is another object of the invention to enable recharging of electrically operated, battery containing toilet articles within the cabinet.

It is a further object of the invention to accommodate toilet articles of different dimensions and configurations when storing, sterilizing, and recharging the same.

Still another object of the invention is to provide illumination within the cabinet.

An additional object of the invention is to provide independent control of sterilizing and illumination.

It is an object of the invention to assure that users are not exposed to UV radiation from the cabinet.

Yet another object of the invention is to enable recharging of electrically operated, battery containing appliances from the exterior of the cabinet.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
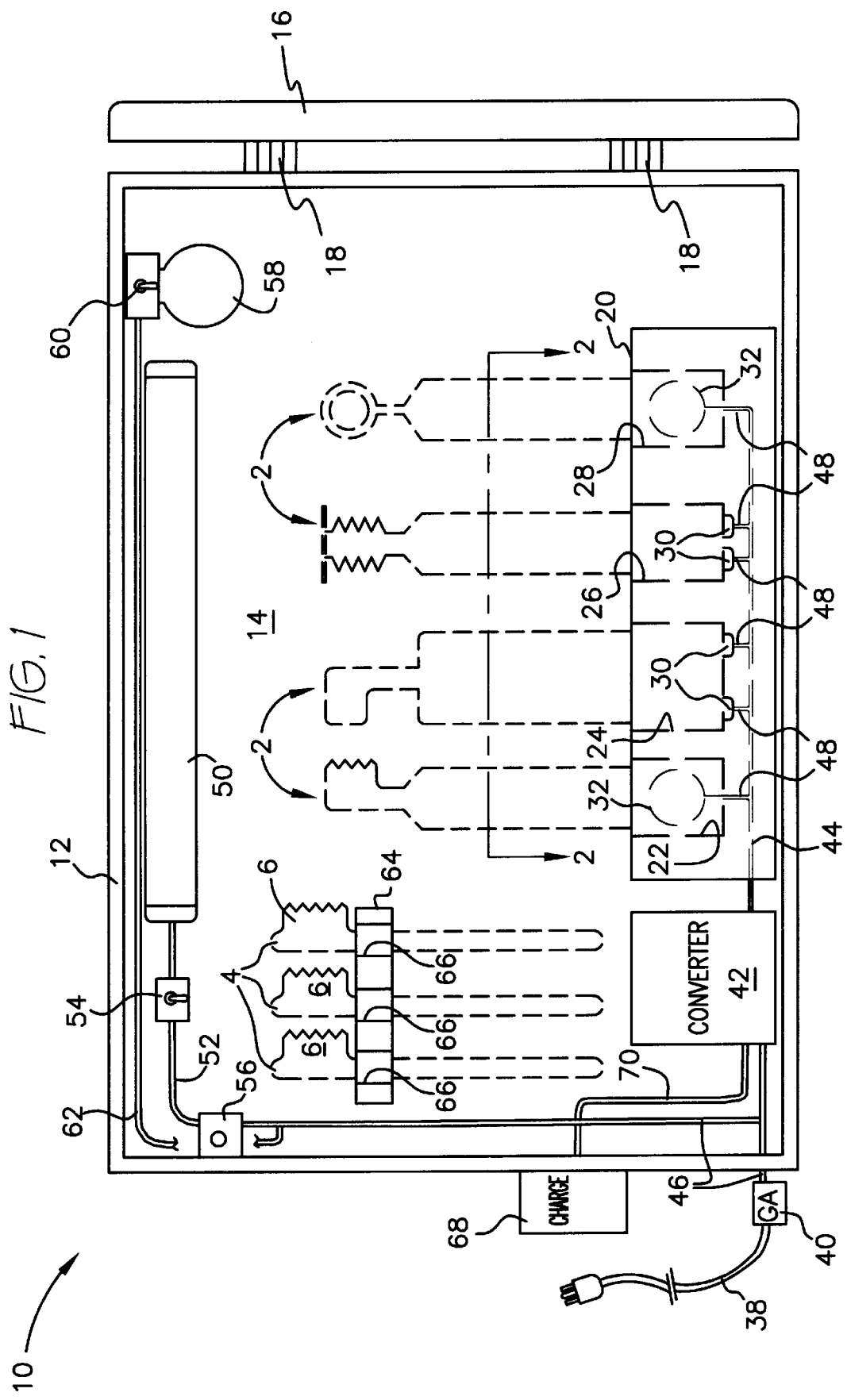
FIG. 1 is a diagrammatic, front elevational view of the invention.

FIG. 1 of the drawings shows novel storage and sterilizing cabinet 10 partially filled with personal toilet articles being stored. In the depiction of FIG. 1, the personal articles include electric toothbrushes 2 and manual toothbrushes 4. Toothbrushes 2, 4 are representative of articles which may be stored, sterilized, and recharged in cabinet 10. Illustratively, other articles may include razors, combs and hair brushes, tweezers, and other implements for personal care.

Cabinet 10 comprises a housing 12 which encloses an internal sterilizing chamber 14. A door 16 is mounted on housing 12 and pivots on piano hinges 18 to move between an open position exposing chamber 14 and a closed position closing chamber 14. A holder 20 is mounted within chamber 14. Holder 20 has four receptacles 22, 24, 26, 28 dimensioned and configured to receive and support toothbrushes 2 or other personal toilet articles. Each receptacle 22, 24, 26 or 28 has associated recharging elements of conventional nature for recharging the rechargeable battery (not separately shown) of its associated toilet article. Receptacles 22, 24, 26, 28 are configured to support the articles in positions such that the recharging elements of cabinet 10 remain in operable proximity to corresponding recharging elements of the toilet articles.

Recharging elements include pairs of exposed electrodes or contacts 30, there being one contact 30 in the pair for each polarity, and covered induction coils 32. Cabinet 10 includes electrical circuitry connected to contacts 30 and coils 32. The electrical circuitry includes a plug 36 and cord 38 extending outside housing 12 for connection to a domestic receptacle (not shown) served with AC electrical power. Cord 38 is preferably protected by a ground fault interrupter 40 disposed serially therein. Power from cord 38 is connected to an AC-to-DC converter 42 which in turn is connected to contacts 30 and coils 32. Conductors, including cord 38, will be understood to include two suitably insulated conductors where required to complete an electrical circuit. Where described as connected, conductors and other conventional electrical components are operably connected, which signifies that the apparatus includes all necessary components required to enable operation of the subject component. Illustratively, insulation, connectors, switches, and other conventional components are encompassed in the foregoing description.

The electrical circuitry has an AC portion 46 to which cord 38 is connected. Converter 40 is operably connected to AC portion 46, and has DC power output conductors 44 connected to the DC output of converter 40, which conductors 44 are operably connected to contacts 30 and coils 32. Output conductors 44 are electrically connected to connection conductors 48, which in turn are connected to the various contacts 30 and coils 32.

Cabinet 10 has a sterilizing lamp 50 of the type capable of emitting ultraviolet (UV) radiation when appropriately energized. Sterilizing lamp 50 has an electrical operating system including conductors 52, a manual switch 54, and a door switch 56. Door switch 56 is a proximity sensing switch or any other type of switch capable of opening or breaking the circuit to lamp 50 when door 16 is in the open position, or not fully closed. In the closed position (not shown), that being sufficiently closed to obstruct UV radiation from passing to the exterior of chamber 14, switch 56 is closed. Switches 54 and 56 are in series, so that lamp 50 operates only when switch 56 senses that door 16 is safely closed and the user has moved switch 54 to the operating or "on" position.

Cabinet 10 has an illumination lamp 58 capable of emitting visible light disposed within sterilizing chamber 14. Lamp 58 is served by its own manual switch 60 disposed to control power from conductors 62 connecting illumination lamp 58 to AC portion 46 of the electrical circuitry.

Cabinet 10 has a rack 64 having a plurality of suitable slots or holes 66 for holding manual toothbrushes 4. Rack 64 is located suitably for exposing bristles 6 of toothbrushes 4 to UV radiation emitted by lamp 50.

Cabinet 10 has a charging receptacle 68 mounted exteriorly on housing 12, and electrical conductors 70 connecting said receptacle 68 to AC-to-DC converter 42.

Figure 2:
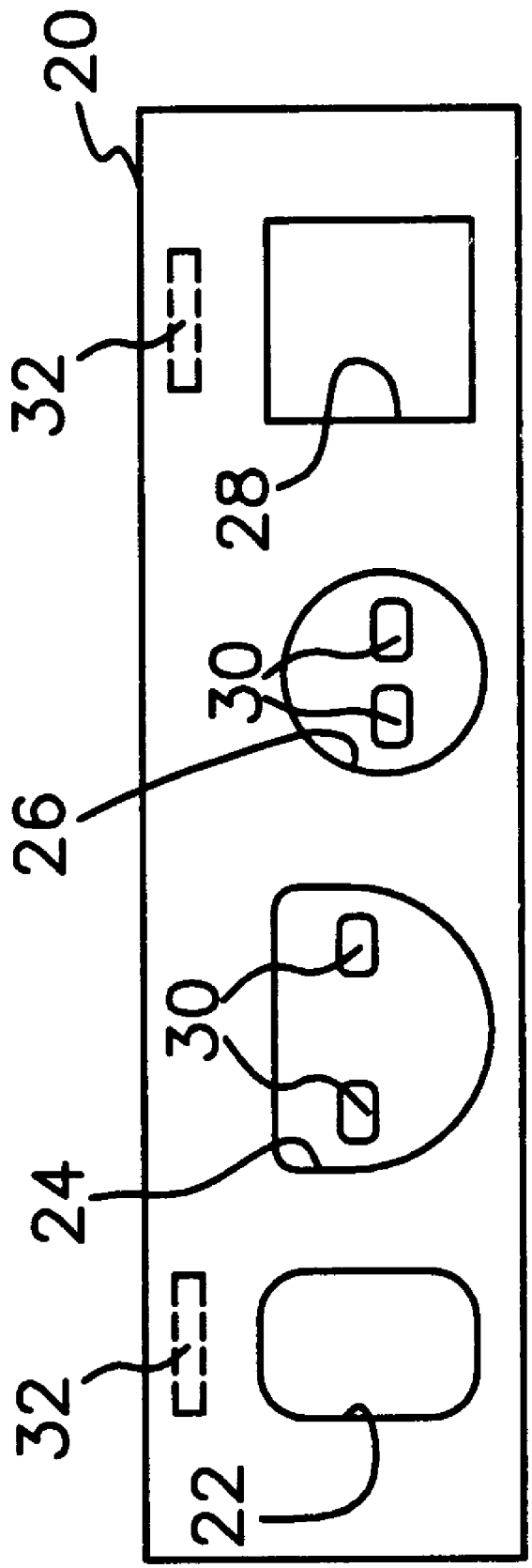
FIG. 2 is a top plan detail view taken along line 2—2 of FIG. 1.

FIG. 2 shows how cabinet 10 can accommodate most, if not all, of the many electrical toothbrushes 2 which are commercially available. Each receptacle 22, 24, 26, or 28 formed in holder 20 has a configuration corresponding to that of one toothbrush 2, the configuration being different from those of other receptacles 22, 24, 26, 28. The configurations illustrated are arbitrarily selected and do not necessarily correspond to those of commercially available electric toothbrushes 2, since design of the latter may change. The actual configurations will be configured and selected to be appropriate for electric toothbrushes 2 actually commercially available to the public. Similarly, recharging elements are representatively illustrated, and may vary from the depictions shown herein.

The present invention is susceptible to variations and modifications which may be introduced without departing from the inventive concept. For example, chamber 14 may be configured to leave unoccupied space, so that other personal articles (not shown) may stored and sterilized therein. Also, microbe destroying agents, such as a microwave generator, apparatus for discharging a gas or other chemical capable of inhibiting microbes, such as formaldehyde, other than lamp 50 may be contained inside sterilizing chamber 14. In a further example, door 16 may be arranged to slide rather than swing open and closed, or may be superseded by two complementing doors (not shown).

It is to be understood that the present invention is not limited to the embodiments described above, but encompasses any and all embodiments within the scope of the following claims.

I claim:

1. A storage and sterilizing cabinet for personal toilet articles, comprising:

a housing enclosing an internal sterilizing chamber, said housing including a door mounted thereon, said door disposed to move between an open position exposing said sterilizing chamber and a closed position closing said sterilizing chamber;

a microbe destroying agent contained inside said sterilizing chamber;

electrical circuitry; and a holder within said internal sterilizing chamber having a plurality of receptacles for receiving and supporting personal toilet articles, including a first receptacle having a first receptacle configuration and a first recharging element electrically connected to said electrical circuitry and a second receptacle having a second receptacle configuration different from that of said first receptacle and a second recharging element electrically connected to said electrical circuitry.

2. The storage and sterilizing cabinet according to claim 1, further comprising a rack having a plurality of slots for holding manual toothbrushes.

3. The storage and sterilizing cabinet according to claim 1, wherein said first recharging element comprises exposed electrodes and said second recharging element comprises a covered induction coil.

4. The storage and sterilizing cabinet according to claim 1, wherein said electrical circuitry has an AC portion and a plug and cord connected to said AC portion, said plug and cord extending outside said housing, an AC-to-DC converter having DC power output conductors, said AC-to-DC converter operably connected to said AC portion, and connection conductors connecting said first recharging element and said second recharging element to said DC power output conductors.

5. The storage and sterilizing cabinet according to claim 4, further comprising a charging receptacle mounted on said housing exteriorly of said sterilizing chamber, and electrical conductors connecting said charging receptacle to said AC-to-DC converter.

6. The storage and sterilizing cabinet according to claim 1, wherein said microbe destroying agent has an electrical operating system connected to said electrical circuitry, and said electrical operating system includes a door switch disposed to sense said open position of said door and to break electrical power from said electrical circuitry to said microbe destroying agent responsive to sensing said open position.

7. The storage and sterilizing cabinet according to claim 1, wherein said microbe destroying agent is a sterilizing lamp capable of emitting ultraviolet radiation.

8. The storage and sterilizing cabinet according to claim 1, further comprising an illumination lamp capable of emitting visible light disposed within said sterilizing chamber, conductors connecting said illumination lamp to said electrical circuitry, and a switch controlling power to said illumination lamp from said electrical circuitry.

9. A storage and sterilizing cabinet for personal toilet articles, comprising:

a housing enclosing an internal sterilizing chamber, said housing including a door mounted thereon, said door disposed to move between an open position exposing said sterilizing chamber and a closed position closing said sterilizing chamber;

a sterilizing lamp capable of emitting ultraviolet radiation contained inside said sterilizing chamber;

electrical circuitry comprising an AC portion and a plug and cord connected to said AC portion, said plug and cord extending outside said housing, an AC-to-DC converter having DC power output conductors, said AC-to-DC converter operably connected to said AC portion;

a holder within said internal sterilizing chamber having a plurality of receptacles for receiving and supporting personal toilet articles, including a first receptacle having a first receptacle configuration and a first recharging element electrically connected to said electrical circuitry and a second receptacle having a second receptacle configuration different from that of said first receptacle and a second recharging element electrically connected to said electrical circuitry, wherein said first recharging element comprises exposed electrodes and said second recharging element comprises a covered induction coil, said electrical circuitry further including connection conductors connecting said first recharging element and said second recharging element to said DC power output conductors;

a rack having a plurality of slots for holding manual toothbrushes;

a charging receptacle mounted on said housing exteriorly of said sterilizing chamber, and electrical conductors connecting said charging receptacle to said AC-to-DC converter;

an illumination lamp capable of emitting visible light disposed within said sterilizing chamber, conductors connecting said illumination lamp to said electrical circuitry, and a switch controlling power to said illumination lamp from said electrical circuitry, wherein said microbe destroying agent has an electrical operating system connected to said electrical circuitry, and said electrical operating system includes a door switch disposed to sense said open position of said door and to break electrical power from said electrical circuitry to said microbe destroying agent responsive to sensing said open position.

* * * * *